United States Patent [19]

Kurz

[11] Patent Number: 4,669,981

[45] Date of Patent: Jun. 2, 1987

[54] LINGUAL ORTHODONTIC APPLIANCE SYSTEM

[76] Inventor: Craven H. Kurz, No. 6 North Star, Apt. 106, Marina del Rey, Calif. 90291

[21] Appl. No.: 420,277

[22] Filed: Sep. 20, 1982

[51] Int. Cl.[4] .............................................. A61C 3/00
[52] U.S. Cl. ........................................................ 433/9
[58] Field of Search ..................... 433/8, 9, 10, 11, 15, 433/16, 17, 18, 24

[56] References Cited

U.S. PATENT DOCUMENTS

| | | | |
|---|---|---|---|
| 3,477,128 | 11/1969 | Andrews | 433/16 |
| 3,842,503 | 10/1974 | Wildman | 433/24 |
| 3,922,787 | 12/1975 | Fischer et al. | 433/15 |
| 4,209,906 | 7/1980 | Fujita | 433/11 |
| 4,216,583 | 8/1980 | Reynolds | 433/9 |

*Primary Examiner*—John J. Wilson
*Attorney, Agent, or Firm*—Keith D. Beecher

[57] ABSTRACT

A direct-bonded fixed lingual orthodontic appliance system is provided which comprises a plurality of metal or plastic attachments which are designed to be cemented directly to the lingual surfaces of the teeth of a patient, of either the mandibular or maxillary arches, and an arch wire intercoupling the attachments extending around the lingual side of the teeth. The surface of the base of each of the attachments contacting the corresponding tooth is particularly configured so as to have intimate contact with the tooth. The attachments are shaped to provide maximum inter-bracket space, especially for the mandibular anterior teeth, so as to facilitate the insertion and securement of the arch wire. The wider the interbracket space the more expression of the arch wire can be achieved resulting in gentler pressures being applied at longer force moments. The thickness of each bracket combined with base thickness is designed to reduce the requirement for in-and-out bends in the arch wire. The attachments are also constructed to incorporate built-in torque and tip angulation correction properties for tooth positioning.

4 Claims, 7 Drawing Figures

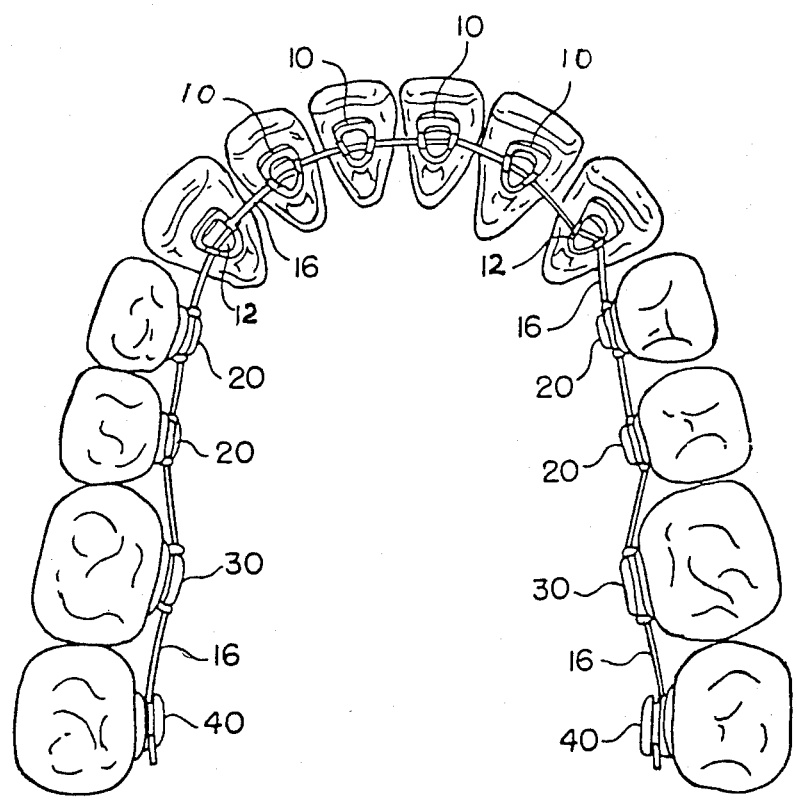

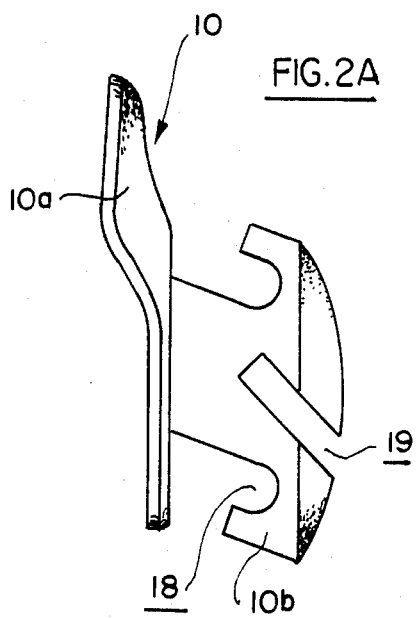
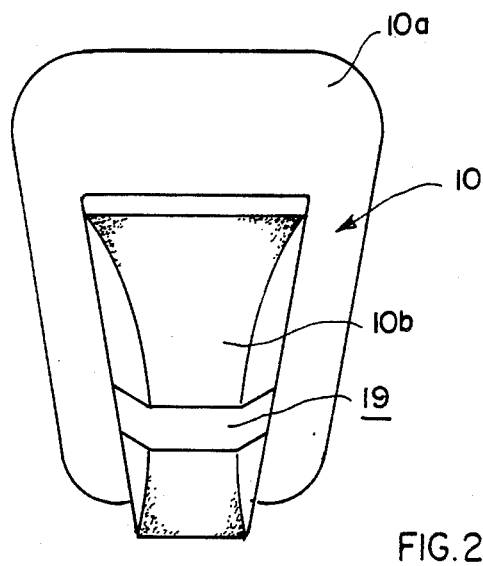
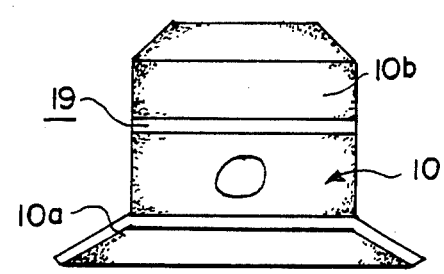
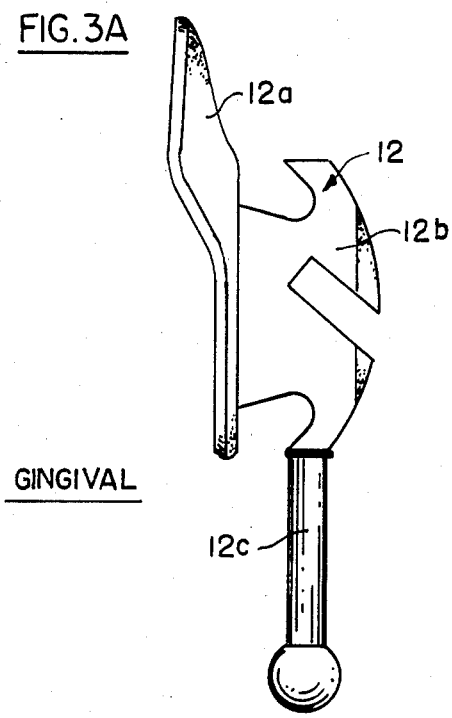
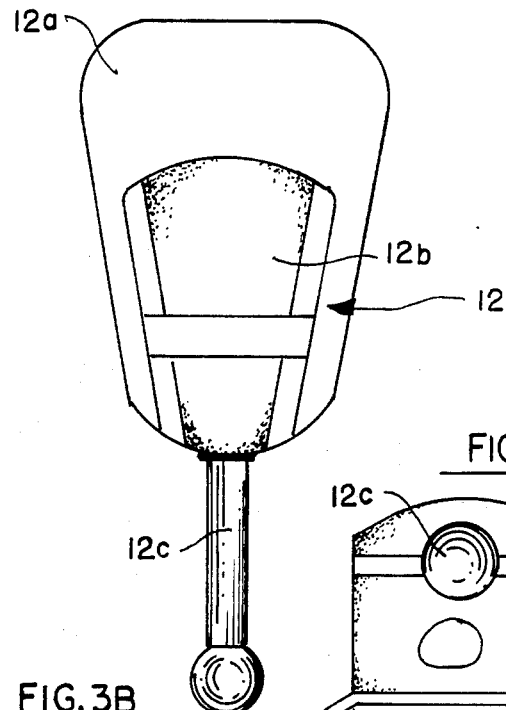
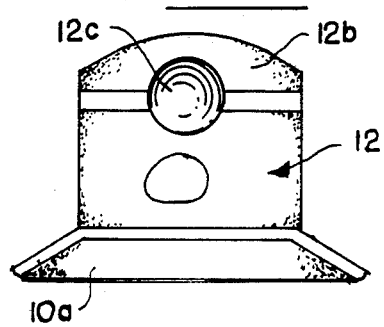

LINGUAL ORTHODONTIC APPLIANCE SYSTEM

BACKGROUND OF THE INVENTION

The prior art arch wire fixed orthodontic appliance systems usually comprise a plurality of attachments in the form of brackets and tubes which are cemented or banded to the labial and buccal surfaces of the respective teeth around both arches, and which, in each instance, are intercoupled by an arch wire extending around the external surfaces of the teeth. Although the prior art appliance systems are effective, they are unsightly and embarrassing to the wearer.

A direct bonded orthodontic arch wire appliance system is described in Copending application Ser. No. 301,452 filed in the name of the present inventor on Sept. 14 1981, which issued June 7, 1983 as U.S. Pat. No. 4,368,908 in which the attachments are configured to be cemented to the lingual surfaces of the teeth, and the system is virtually invisible.

The attachments of the appliance system of the present invention are generally similar to the attachments described in the copending application, and are further constructed, shaped and configured to facilitate the insertion and removal of the arch wire.

BRIEF DESCRIPTION OF THE DRAWINGS

FIG. 1 is a plan view of the mandibular arch of a patient, showing a direct bonded fixed lingual orthodontic arch wire appliance system, such as the system described in the copending application;

FIGS. 2A, 2B and 2C represent three views of a lingual bracket suitable for use with the central lateral anterior incisors in the arch of FIG. 1; and FIGS. 3A, 3B and 3C represent three views of a lingual bracket suitable for use with the cuspids, or canines, of the arch of FIG. 1.

DETAILED DESCRIPTION OF THE ILLUSTRATED EMBODIMENT

The bases of the attachments of the lingual appliance system of FIG. 1 are constructed to incorporate a straight wire concept by providing an individualized thickness for the attachments so that a straight contoured arch wire 16 will not require in-and-out bends, as it is inserted into the attachments. The attachments also incorporate a special built-in angulation mesio-distally, and a built-in angulation bucco-lingually and labio-lingually for that purpose.

In the representation of FIG. 1, a direct bonded fixed lingual wire appliance system is shown with the attachments of the system being adhesively affixed to the lingual surfaces of the teeth forming the mandibular arch.

The orthodontic appliance system of FIG. 1 includes a plurality of attachments, in the form of brackets 10, shown in detail in FIGS. 2A, 2B and 2C. These brackets are adhesively attached to the lingual surfaces of the central and lateral anterior incisors. The system of FIG. 1 also includes attachments in the form of brackets 12, which are shown in detail in FIGS. 3A, 3B and 3C, and which are cemented to the lingual surfaces of the cuspids (canines).

As shown in FIGS. 2A, 2B, 2C and 3A, 3B, 3C, the configuration of the brackets for the mandibular central incisors, lateral incisors, and cuspids, is essentially the same. The only difference is the size of the brackets used in conjunction with the different teeth. As illustrated in FIGS. 2A, 2B, 2C and 3A, 3B, 3C, the external edges of the brackets are rounded to avoid trauma to the tongue. There are no sharp corners, and the bracket profile is kept intentionally low so as to avoid crowding of the tongue space.

As described in detail in the copending application Ser. No. 301,452, the bases of attachments 10 and 12 for the central incisors, lateral incisors and cuspids, as shown in FIGS. 2A, 2B, 2C and 3A, 3B, 3C are convex gingivally and straight incisally. The base is convex mesio-distally to fit into the marginal ridges of the teeth. The gingival portion of the base is tapered to conform with the gingival taper of the tooth while wider at the incisal portion as is the incisal portion of the tooth. The bases of the attachments are designed to fit between the lingual ridges of the teeth in intimate contact with the lingual tooth surface. This shaping of the bases allows for optimal bonding of the attachments to the teeth, and for a uniform fit of the attachments onto the lingual surfaces of the teeth.

As shown in FIGS. 2A, 2B, 2C, attachment 10 includes a base portion 10a which is adhesively attached to the lingual surface of the tooth. The attachment also includes a bracket portion 10b which is integral with the base 10a, but of somewhat smaller transverse dimensions than the base. The portion 10b extends outwardly from the base. Moreover, portion 10b is tapered towards its lower edge, as shown, in order to provide the orthodontist with maximum possible working space for the insertion of the arch wire 16 into a transverse slot 19, and for securing the arch wire in the slot. A peripheral groove 18 extends between bracket portion 10b and base 10a for receiving a ligature 14 for holding the arch wire within the transverse slot. Each bracket may have a vertical slot. This vertical slot is utilized at times to aid in the engagement of the arch wire, and at other times it is used for the insertion of an auxiliary spring to facilitate rotation and uprighting of the tooth.

The attachment 12, as shown in FIGS. 3A, 3B and 3C is similarly configured; with the bracket portion 10b also being tapered, as shown. A hook 12c may be provided on the bracket to facilitate the attachment of the ligature and serves to act as an anchor or attachment for the elastics used to move the teeth.

A specific angulation for the transverse slot of the brackets, as indicated by the following tables, is designed into the appliance so that the appliance has a built-in tip, torque and in-out requirements.

| Bracket 10 | | Bracket 12 | |
|---|---|---|---|
| Torque: | +46° | Torque: | +40° |
| Tip: | +2° | Tip: | +9° |
| Rotation: | 0° | Rotation: | +4° |
| In-out: | 0° | In-out: | 0° |
| Slot size: | .018 inches | Slot size: | .018 inches |

As stated above, the base of each attachment has a thickness such that no in-and-out bends are required of the contoured arch wire 16.

The appliances of the invention may be all metal, all plastic, metal brackets with laminated plastic bases, or part metal and part plastic brackets with plastic bases. The all metal attachment has the advantage of being the strongest design and the metal arch wire moves with less friction in a metal slot reducing any drag and loss of efficienty during orthodontic movements. The metal attachment must have a bonding base, so that it may be adhesively attached to the tooth's surface. The all-plastic attachment is not as strong as the all-metal attachment.

The invention provides, therefore, an orthodontic attachment having a tapered base having a decreasing transverse dimension from its incisal end to gingival end. This is most important, since without this feature the interbracket space on a lingual appliance is so reduced that this feature is required to facilitate arch wire placement, and also the greater the length of the wire between brackets the longer the movement moment of the arch wire is expressed to translate greater distance of movement and gentler movement to the teeth.

It will be appreciated that while particular embodiments of the invention have been shown and described, modifications may be made, and it is intended in the following claims to cover all modifications which come within the spirit and scope of the invention.

What is claimed is:

1. An attachment for use in a fixed lingual arch wire appliance system to be attached to the lingual surface of an anterior incisor, said attachment having a base to be adhesively attached to the tooth, and said base being tapered to have a decreasing transverse dimension being shaped to fit between the marginal lingual ridges of the from the incisal end to the gingival end thereof, and said base tooth to fit the anatomy of the lingual surface thereof, and said attachment including a bracket attached to the base, said bracket being tapered to have a decreasing transverse dimension from the incisal end to the gingival end thereof to facilitate the placement of the arch wire and increase the length of the force moment of the arch wire being used to move the tooth, said bracket having a transverse channel extending thereacross for receiving an arch wire, said channel having a particular buccal-lingual depth, torque angle, tip angle and rotation angle, to accept an arch wire without in-and-out bend requirements.

2. The attachment defined in claim 1, in which said bracket has rounded edges and corners to prevent trauma of the tongue.

3. The system defined in claim 1, in which the transverse channel of said bracket has the following parameters: torque +46°, tip +2°, rotation 0°.

4. The system defined in claim 1, in which the transverse channel of said bracket has the following parameters: torque +40°, tip +9°, rotation +4°.

* * * * *